United States Patent
Kurihara et al.

(10) Patent No.: US 11,534,241 B2
(45) Date of Patent: Dec. 27, 2022

(54) MEDICAL MANIPULATOR SYSTEM AND IMAGE DISPLAY METHOD THEREFOR

(71) Applicant: OLYMPUS CORPORATION, Tokyo (JP)

(72) Inventors: Kyohei Kurihara, Tokyo (JP); Mitsuaki Hasegawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1207 days.

(21) Appl. No.: 16/010,559

(22) Filed: Jun. 18, 2018

(65) Prior Publication Data

US 2018/0296280 A1    Oct. 18, 2018

Related U.S. Application Data

(63) Continuation of application No. PCT/JP2015/086115, filed on Dec. 24, 2015.

(51) Int. Cl.
*A61B 1/00*        (2006.01)
*A61B 34/20*       (2016.01)
(Continued)

(52) U.S. Cl.
CPC .......... *A61B 34/20* (2016.02); *A61B 1/00004* (2013.01); *A61B 1/0005* (2013.01);
(Continued)

(58) Field of Classification Search
CPC . A61B 34/20; A61B 1/00004; A61B 1/00006; A61B 1/00009; A61B 1/00045;
(Continued)

(56) References Cited

U.S. PATENT DOCUMENTS 8,556,803 B2 * 10/2013 Shigeta .............. G02B 23/2484
600/173
2004/0204627 A1   10/2004 Furukawa
(Continued)

FOREIGN PATENT DOCUMENTS

EP         2186466 A1    5/2010
JP      H09-149876 A     6/1997
(Continued)

OTHER PUBLICATIONS

International Search Report dated Feb. 9, 2016 issued in PCT/JP2015/086115.

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

A medical manipulator system includes: an endoscope; a first manipulator equipped with a first treatment tool at a distal end thereof; a second manipulator equipped with a second treatment tool at a distal end thereof; a display for a user to view; and a controller configured to generate an image to be displayed on the display. The controller is configured to: acquire a first image taken by the endoscope, the first image contains the first treatment tool; and in response to determining that the second treatment tool does not exist in the first image: calculate a relative distance and a relative direction between the first treatment tool and the second treatment tool; generate a second image showing the relative distance and the relative direction between the first treatment tool and the second treatment tool; and send the first image and the second image to the display.

8 Claims, 8 Drawing Sheets

(51) Int. Cl.
*A61B 34/30* (2016.01)
*A61B 90/00* (2016.01)
*A61B 1/005* (2006.01)
*A61B 1/04* (2006.01)
*A61B 34/00* (2016.01)
*A61B 17/00* (2006.01)

(52) U.S. Cl.
CPC ...... *A61B 1/00006* (2013.01); *A61B 1/00009* (2013.01); *A61B 1/00045* (2013.01); *A61B 1/0052* (2013.01); *A61B 1/00149* (2013.01); *A61B 1/04* (2013.01); *A61B 17/00234* (2013.01); *A61B 34/30* (2016.02); *A61B 34/74* (2016.02); *A61B 90/361* (2016.02); *A61B 2034/2046* (2016.02); *A61B 2034/2057* (2016.02); *A61B 2034/2065* (2016.02); *A61B 2034/301* (2016.02); *A61B 2090/364* (2016.02); *A61B 2090/368* (2016.02)

(58) Field of Classification Search
CPC . A61B 1/0005; A61B 1/00149; A61B 1/0052; A61B 1/04; A61B 17/00234; A61B 34/30; A61B 34/74; A61B 90/361; A61B 2034/2046; A61B 2034/2057; A61B 2034/2065; A61B 2034/301; A61B 2090/364; A61B 2090/368; A61B 34/77; B25J 3/00; B25J 9/1664; B25J 19/06; G02B 27/0149
USPC .................................................. 600/117, 118
See application file for complete search history.

(56) References Cited

U.S. PATENT DOCUMENTS

| | | | |
|---|---|---|---|
| 2005/0033117 A1* | 2/2005 | Ozaki | A61B 1/042 |
| | | | 600/117 |
| 2005/0182296 A1 | 8/2005 | Furukawa | |
| 2008/0004603 A1* | 1/2008 | Larkin | A61B 34/10 |
| | | | 606/1 |
| 2009/0192523 A1* | 7/2009 | Larkin | B25J 9/1671 |
| | | | 606/130 |
| 2009/0248036 A1* | 10/2009 | Hoffman | A61B 1/00188 |
| | | | 606/130 |
| 2010/0217075 A1 | 8/2010 | Shigeta | |
| 2014/0005475 A1* | 1/2014 | Song | A61B 1/045 |
| | | | 600/109 |
| 2014/0135792 A1 | 5/2014 | Larkin et al. | |
| 2014/0371527 A1 | 12/2014 | Sato | |

FOREIGN PATENT DOCUMENTS

| | | |
|---|---|---|
| JP | 2001-150368 A | 6/2001 |
| JP | 3376029 B2 | 2/2003 |
| JP | 2004-105533 A | 4/2004 |
| JP | 2007-029232 A | 2/2007 |
| JP | 2007-152027 A | 6/2007 |
| JP | 2009-542362 A | 12/2009 |
| JP | 2015-000093 A | 1/2015 |
| WO | WO 2008/002830 A2 | 1/2008 |
| WO | WO 2009/084345 A1 | 7/2009 |

* cited by examiner

MEDICAL MANIPULATOR SYSTEM AND IMAGE DISPLAY METHOD THEREFOR

This is a continuation of International Application PCT/JP2015/086115, with an international filing date of Dec. 24, 2015, which is hereby incorporated by reference herein in its entirety.

TECHNICAL FIELD

The present invention relates to a medical manipulator system and an image display method therefor.

BACKGROUND ART

One known example of a medical manipulator system equipped with an endoscope and a manipulator having a treatment tool attached thereto is a medical manipulator system with which, in displaying an endoscopic image showing an affected area and a distal end portion of a treatment tool, said endoscopic image being acquired via the endoscope, images of other treatment tools that exist outside the field of view of the endoscope are superimposed and displayed around the endoscopic image (for example, refer to PTL 1). Each of the treatment tools outside the field of view is indicated by an icon that lies at a circumferential position of the endoscopic image so as to show the direction in which the treatment tool exists.

CITATION LIST

Patent Literature

{PTL 1}
U.S. Patent Application Publication No. 2014/0135792

SUMMARY OF INVENTION

One aspect of the present invention is directed to a medical manipulator system including: an endoscope; a first manipulator equipped with a first treatment tool at a distal end thereof; a second manipulator equipped with a second treatment tool at a distal end thereof; a display for a user to view; and a controller configured to generate an image to be displayed on the display, wherein the controller is configured to: acquire a first image taken by the endoscope, the first image containing the first treatment tool; and in response to determining that the second treatment tool does not exist in the first image: calculate a relative distance and a relative direction between the first treatment tool and the second treatment tool; generate a second image showing the relative distance and the relative direction between the first treatment tool and the second treatment tool; and send the first image and the second image to the display.

Another aspect of the present invention is directed to a method for controlling a medical manipulator system including: acquiring a first image taken by an endoscope, the first image containing a first treatment tool of a first manipulator; and in response to determining that a second treatment tool of a second manipulator does not exist in the first image: calculating a relative distance and a relative direction between the first treatment tool and the second treatment tool, generating a second image showing the relative distance and the relative direction between the first treatment tool and the second treatment tool, and sending the first image and the second image to a display.

Another aspect of the present invention is directed to a controller for a medical manipulator system including: one or more processors; wherein one or more processors configured to: acquire a first image taken by an endoscope, the first image containing a first treatment tool of a first manipulator; and in response to determining that a second treatment tool of a second manipulator does not exist in the first image: calculate a relative distance and a relative direction between the first treatment tool and the second treatment tool, generate a second image showing the relative distance and the relative direction between the first treatment tool and the second treatment tool, and send the first image and the second image to a display.

DESCRIPTION OF EMBODIMENTS

A medical manipulator system 1 according to an embodiment of the present invention will now be described with reference to the drawings.

Figure 1:
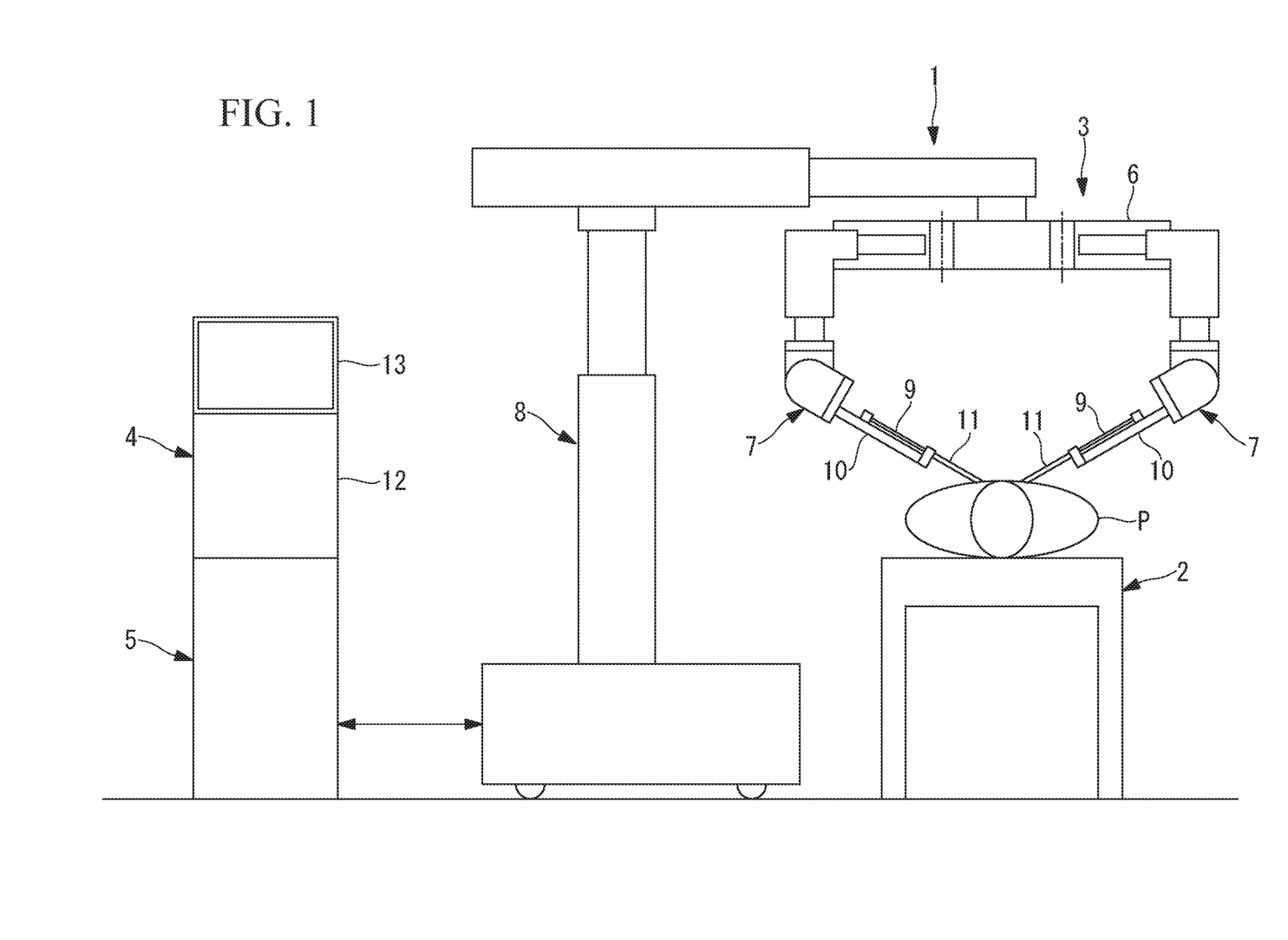
FIG. 1 is an overall structural diagram of a medical manipulator system according to one embodiment of the present invention.

As illustrated in FIG. 1, the medical manipulator system 1 of this embodiment includes a manipulator unit 3 disposed at the side of a bed 2 on which a patient P is laid, an operation unit 4 operated by the user, and a controller 5.

The manipulator unit 3 includes, for example, a base portion 6 disposed above the bed 2 and separated from the bed 2 by a space, manipulators 7 that extend radially outward from the base portion 6, and a base driving portion 8 that supports the base portion 6 so that the base portion 6 can move in at least one of a horizontal direction and a vertical direction.

The base driving portion 8 can three-dimensionally adjust the position of the base portion 6 with respect to the patient P. The base driving portion 8 may be of a type that stands on the floor from the side of the bed 2 or of a type that is fixed to the ceiling.

Each of the manipulators 7 is a multijoint manipulator in which multiple links are connected through multiple joints, and a tool holder 10 for supporting a treatment tool 9 is disposed at the distal end of each manipulator 7. The manipulator 7 can adjust the positions and orientations of the treatment tool 9, the endoscope (not illustrated), and a trocar 11 supported on the tool holder 10 by moving the joints.

The operation unit 4 includes an operation input portion 12 operated by the user, and a monitor (display unit) 13 that displays an image of the inside of the body of the patient P obtained through the endoscope attached to one of the manipulators 7. The user can view, through the image of the inside of the body of the patient P displayed on the monitor 13, the affected area and the distal end portion of the treatment tool 9 attached to one of the manipulators 7, and, at the same time, can operate the operation input portion 12 so as to operate the manipulator 7 and the treatment tool 9 to treat the affected area.

Figure 2:
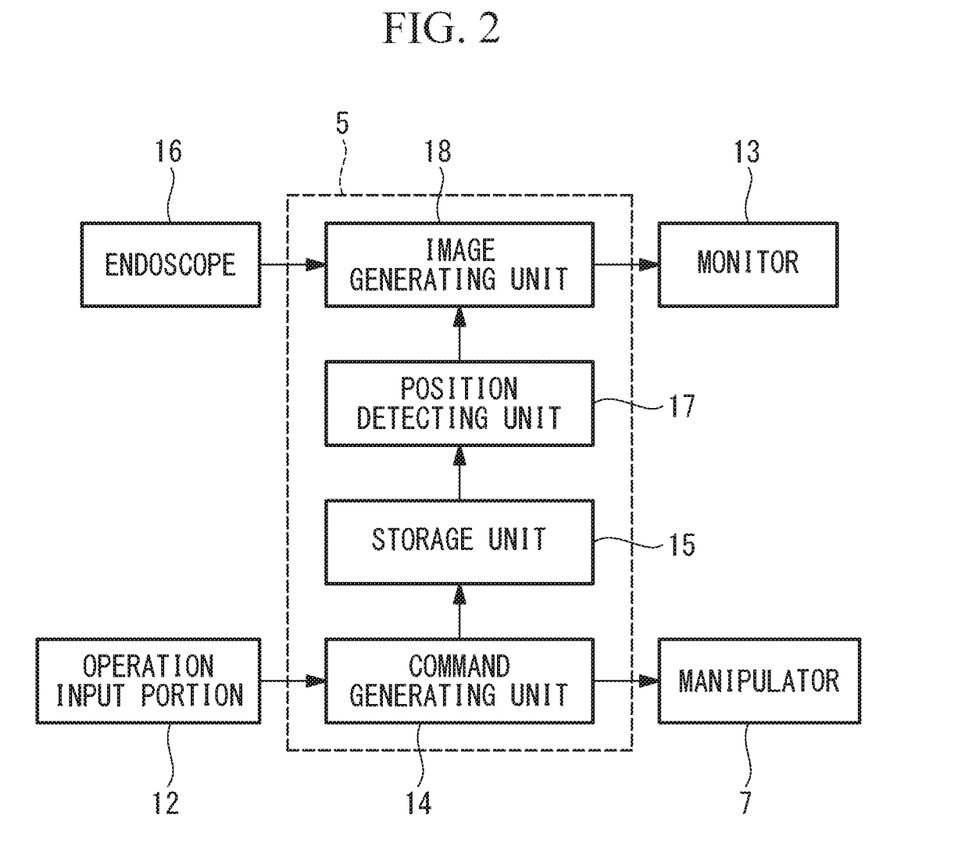
FIG. 2 is a block diagram illustrating the medical manipulator system illustrated in FIG. 1.

As illustrated in FIG. 2, the controller 5 includes a command generating unit 14, a storage unit 15, a position detecting unit 17, and an image generating unit 18. The command generating unit 14 is configured to generate operation commands for operating the manipulators 7 and the treatment tools 9 on the basis of the operation inputs at the operation input portion 12. The storage unit 15 is configured to store the operation commands for the manipulators 7 generated in the command generating unit 14. The position detecting unit 17 is configured to detect, on the basis of the operation commands stored in the storage unit 15, the field of view of the endoscope 16 attached to the manipulator 7, and the positions of the treatment tools 9. The image generating unit 18 is configured to generate a composite image on the basis of the field of view of the endoscope 16 and the positions of the treatment tool 9 detected with the position detecting unit 17, and the image acquired through the endoscope 16.

Figure 3A:
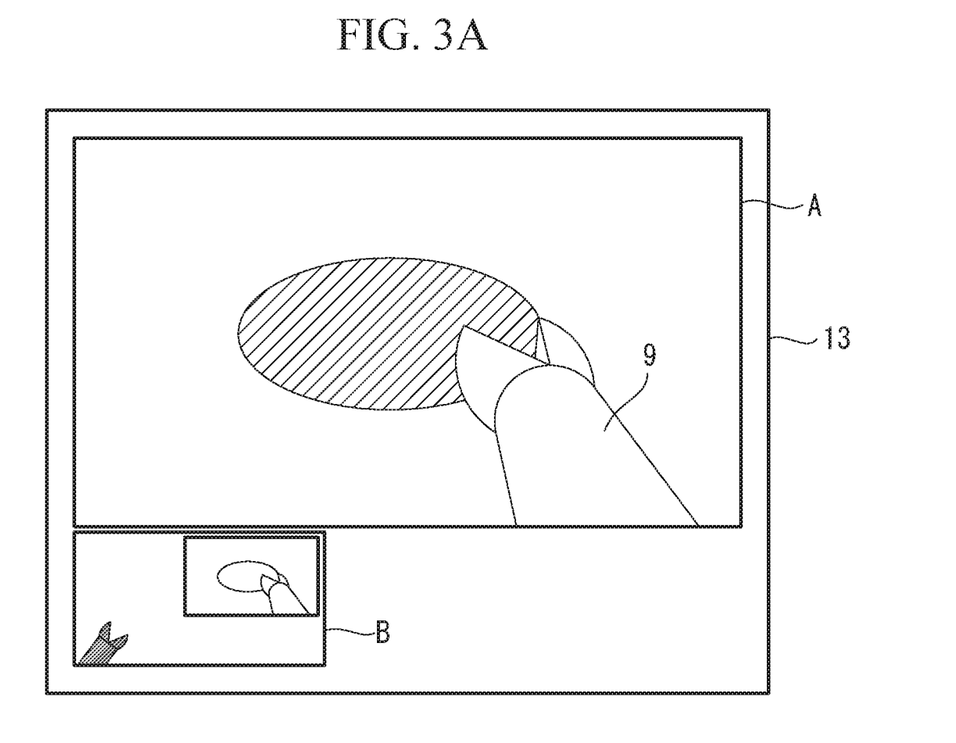
FIG. 3A is a diagram illustrating one example of a composite image generated in the image generating unit inside a controller of the medical manipulator system illustrated in FIG. 2.
Figure 3B:
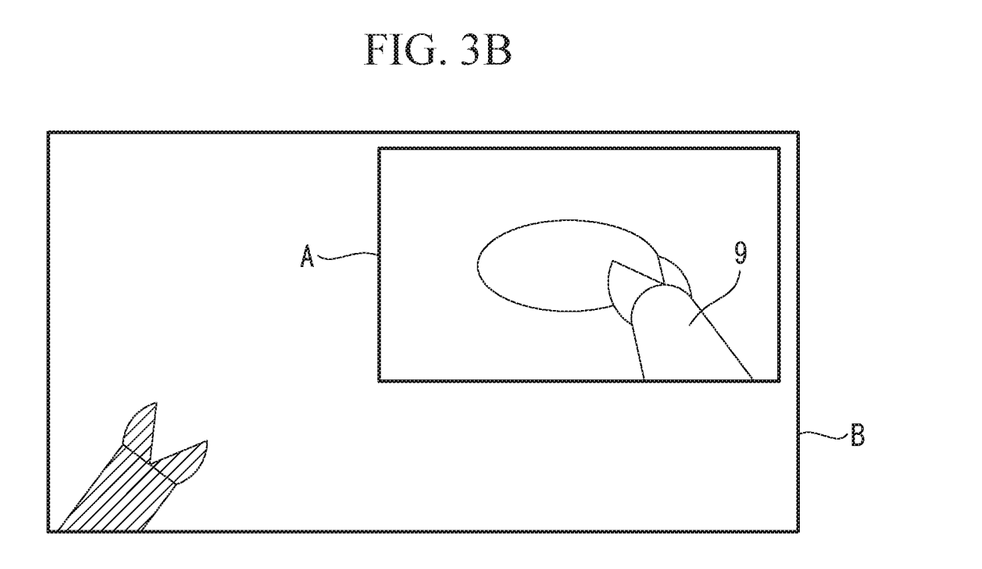
FIG. 3B is a diagram illustrating one example of a second image contained in the composite image illustrated in FIG. 3A.

The image generating unit 18 determines whether any of the treatment tools 9 attached to the manipulators 7 is outside the field of view of the endoscope 16. When any of the treatment tools 9 is outside the field of view, the image generating unit 18 calculates the relative distance and direction of that treatment tool 9 with respect to the field of view of the endoscope 16. Moreover, as illustrated in FIG. 3B, the image generating unit 18 generates a copy (viewing range) of a first image A, which is an image within the field of view of the endoscope 16, and a second image B that includes an icon of the treatment tool 9 disposed at the calculated distance and direction with respect to the viewing range. As illustrated in FIG. 3A, the image generating unit 18 generates a composite image by combining the first image A within the field of view of the endoscope 16 acquired through the endoscope 16 and the second image B of the treatment tool 9 outside the field of view, and sends the generated composite image to the monitor 13.

Figure 3C:
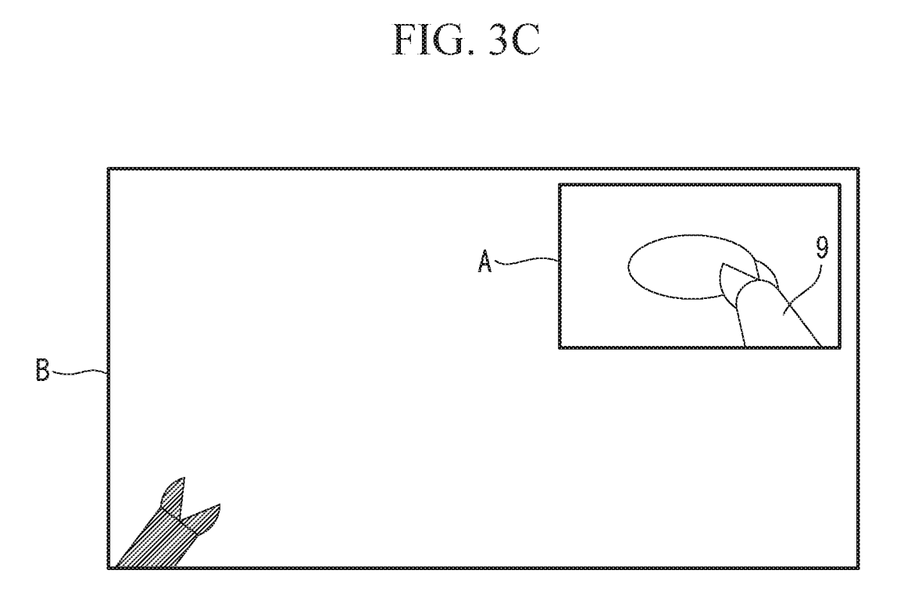
FIG. 3C is a diagram illustrating another example of the second image contained in the composite image illustrated in FIG. 3A.

As illustrated in FIG. 3A, the second image B is set to have a particular scale with respect to the first image A, and the viewing range and the icon of the treatment tool 9 in the second image B are generated at a scale reduced based on the distance of the treatment tool 9 from the viewing range. In other words, the scale of the image in FIG. 3B in which the treatment tool 9 outside the field of view is close to the viewing range is set to be larger than the scale of the image in FIG. 3C in which the treatment tool 9 outside the field of view is far from the viewing range. In this manner, the user can intuitively recognize, from the positional relationship between the viewing range and the icon of the treatment tool 9 in the second image B, how far and in which direction the treatment tool 9 outside the field of view is with respect to the field of view.

Moreover, as illustrated in FIG. 3A, by setting the scale of the second image B sufficiently smaller than that of the first image A, the size of the first image A acquired through the endoscope need not be excessively reduced, and thus the endoscopic image viewed during the treatment can be displayed widely to improve the ease of treatment.

The effects of the medical manipulator system 1 according to this embodiment configured as described above are as follows.

According to the medical manipulator system 1 of this embodiment, the patient P is laid on the bed 2, and trocars 11 are disposed to penetrate into the abdomen of the patient P, for example. After the distal end of the treatment tool 9 is placed inside the body through one of the trocars 11, the trocar 11 and the treatment tool 9 exposed from the body are fixed to the distal end the tool holder 10 of one of the manipulators 7. In the same manner, the distal end of the endoscope 16 is placed inside the body through another one of the trocars 11, which have been placed to penetrate into the abdomen of the patient P, and then the trocar 11 and the endoscope 16 exposed from the body are fixed to the tool holder 10 of another one of the manipulators 7.

Figure 4:
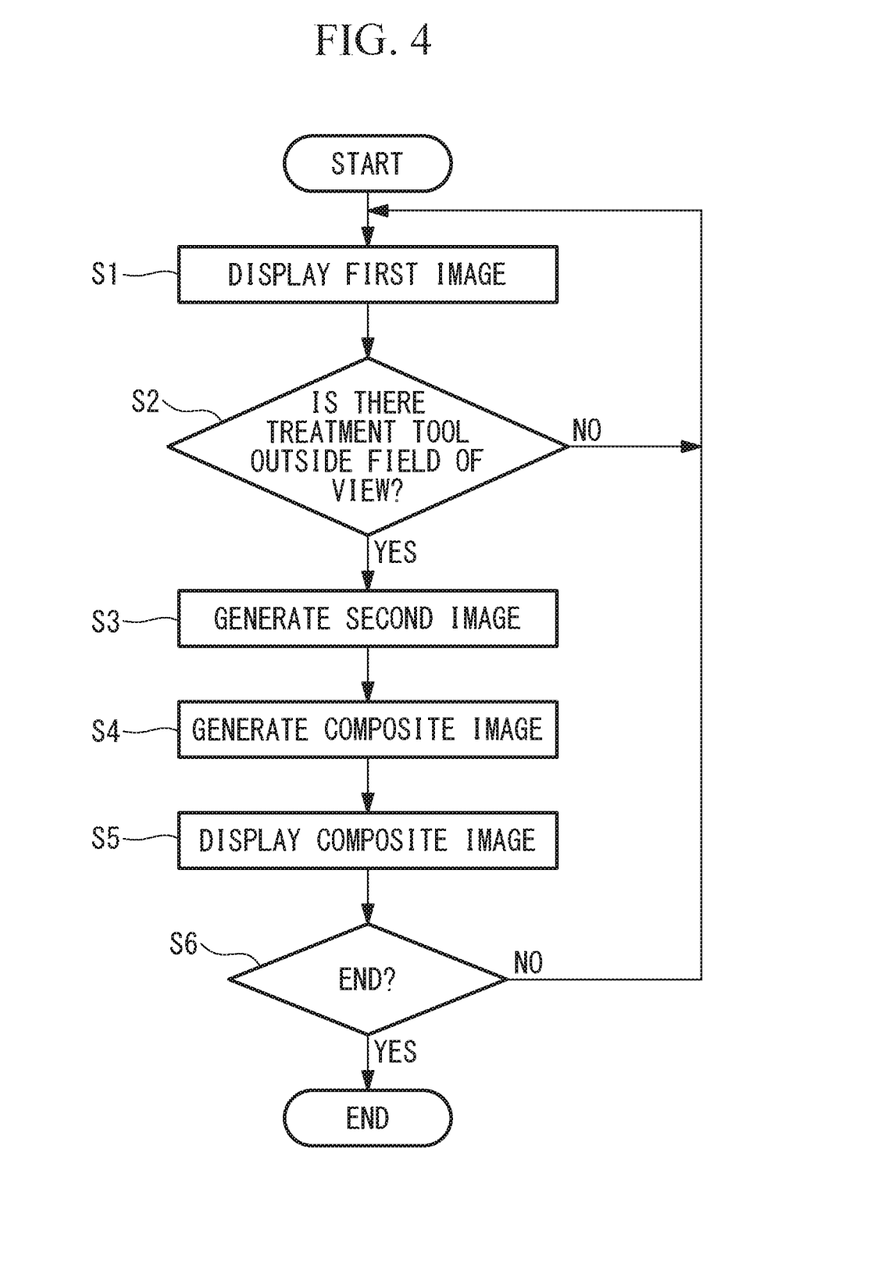
FIG. 4 is a flowchart illustrating an image display method for the medical manipulator system according to one embodiment of the present invention.

The image display method for the medical manipulator system 1 will now be described with reference to FIG. 4. In this state, a first image acquired through the endoscope 16 and showing the inside of the body of the patient P and the distal end portion of the treatment tool 9 disposed in the viewing range of the endoscope 16 is displayed on the monitor 13 of the operation unit 4 (step S1). At this point of time, the user starts coordination of the operation unit 4 and the manipulator unit 3, and operates the operation input portion 12 so that the controller 5 generates an operation command according to the operation input and so that the affected area inside the body of the patient P can be treated by the operation of the manipulator 7 and the treatment tool 9.

In this case, as illustrated in FIG. 2, the position detecting unit 17 in the controller 5 detects, on the basis of the operation command information stored in the storage unit 15 and directed to the manipulators 7, the positions of the treatment tools 9 and the field of view of the endoscope 16 fixed to the tool holder 10 of the manipulator 7. The image generating unit 18 then determines whether the detected position of each treatment tool 9 is within the field of view of the endoscope 16 (step S2). If any of the treatment tools 9 is outside the field of view, a second image B is generated (step S3), and, at the same time, a composite image is generated by combining the first image A and the second image B (step S4) and is displayed on the monitor 13 (step S5), as illustrated in FIG. 3A.

If all of the treatment tools 9 are outside the field of view, the steps starting from step S1 are repeated, and the first image A on the monitor 13 is updated.

When a composite image is displayed, it is determined whether or not to terminate display of the composite image (step S6), and, if the display is not to be terminated, the steps starting from step S1 are repeated.

In this manner, the user can instantly recognize, through the distance and direction between the viewing range and the treatment tool 9 indicated by the icon in the second image B, whether or not the treatment tool 9, which is outside the field of view of the endoscope 16 and thus does not appear in the first image A, is close to the field of view of the endoscope 16. When the treatment tool 9 outside the field of view is close to the field of view of the endoscope 16, the manipulator 7 to be operated can be switched so that the treatment tool 9 outside the field of view can be moved to be within the field of view of the endoscope 16.

In contrast, when the treatment tool 9 outside the field of view is far from the field of view of the endoscope 16, it is possible that the treatment tool 9 outside the field of view may interfere with body tissue during the process of moving the treatment tool 9 over a long distance without visually monitoring the movement thereof; thus, the user is given a choice of not moving the treatment tool 9 outside the field of view.

In other words, according to the medical manipulator system 1 and the image display method therefor according to this embodiment, the user can easily judge the appropriateness of moving the treatment tool 9 that lies outside the field of view of the endoscope 16.

Note that in this embodiment, the out-of-field treatment tool information is configured so that the icon indicates the relative distance and direction with respect to the viewing range in the second image B; in addition, information regarding whether or not the treatment tool 9 outside the field of view is operable may be included in the out-of-field treatment tool information.

Examples of the information regarding whether or not the treatment tool 9 outside the field of view is operable include information regarding whether or not the manipulator 7 to which the treatment tool 9 outside the field of view is attached is coordinated with the operation unit 4, and whether or not the treatment tool 9 outside the field of view is grasping or retracting the tissue around the affected area.

The case in which the manipulator 7 to which the treatment tool 9 outside the field of view is attached is coordinated with the operation unit 4, the case in which the treatment tool 9 outside the field of view is grasping the tissue around the affected area, and the case in which the treatment tool 9 outside the field of view is retracting the tissue around the affected area may be distinguished from one another by changing the color of the icon indicating the treatment tool 9 outside the field of view, for example.

Figure 5:
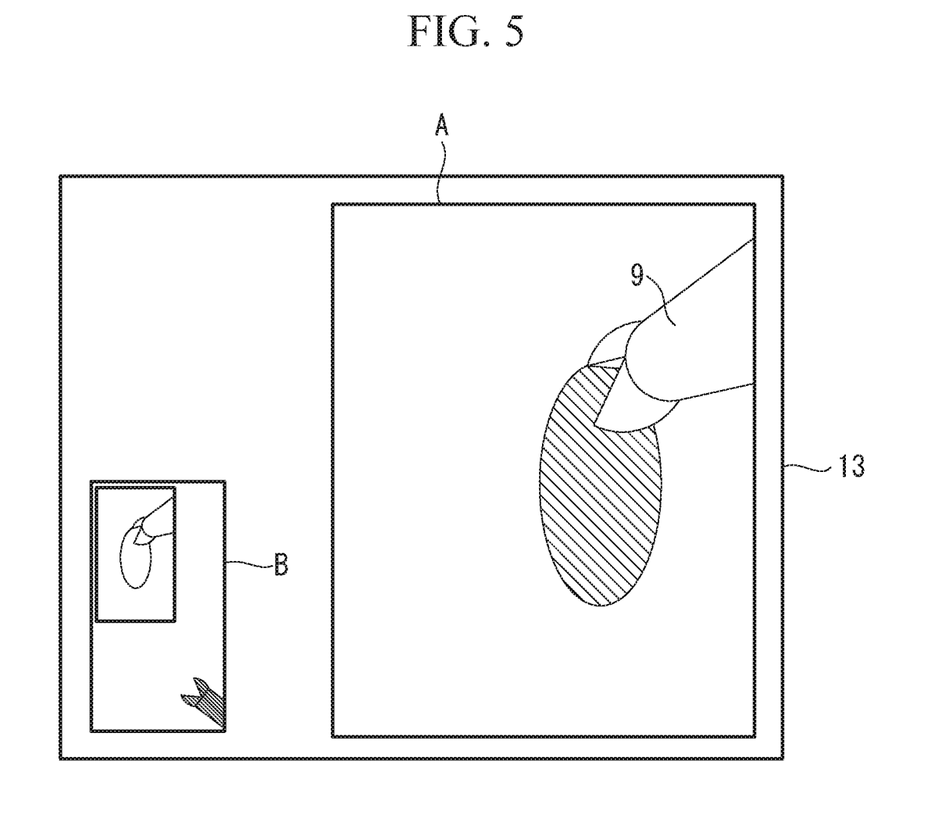
FIG. 5 is a diagram illustrating one example of a composite image generated in the image generating unit when an endoscope is rotated in the medical manipulator system illustrated in FIG. 1.

Preferably, when the first image A indicating the image within the field of view of the endoscope 16 is rotated as illustrated in FIG. 5 by rotating the endoscope 16 through operation of the manipulator 7 supporting the endoscope 16, the second image B is rotated at the same angle. When the direction of the first image A and the direction of the second image B coincide, the user can intuitively judge the position and direction of the treatment tool 9 outside the field of view.

Figure 6:
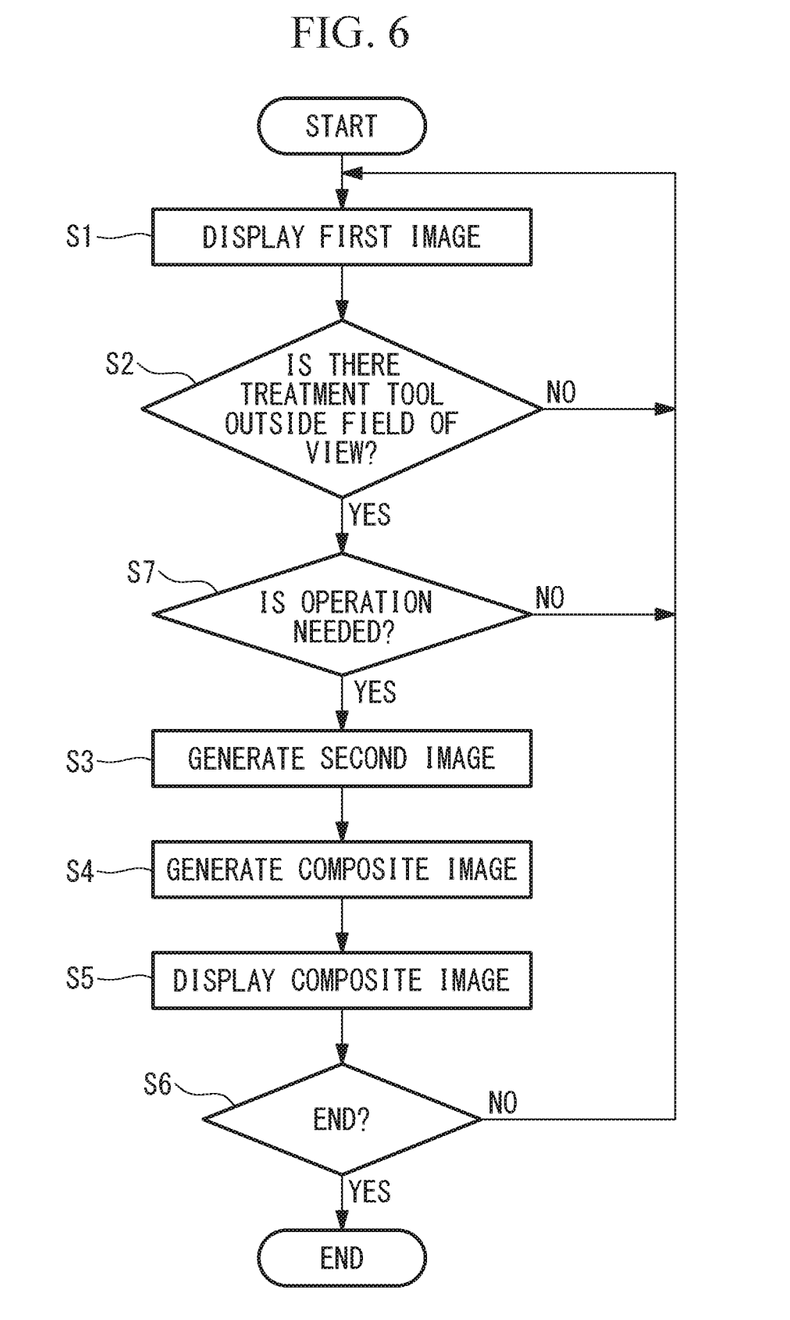
FIG. 6 is a flowchart illustrating an image display method of a modification of the method illustrated in FIG. 4.

In this embodiment, the second image B is always displayed when a treatment tool 9 exists outside the field of view; alternatively, as illustrated in FIG. 6, the second image B may be displayed as needed (step S7).

For example, the second image B may be displayed when it is judged that it is necessary to move the treatment tool 9 outside the field of view, such as when the coordination between the manipulator 7 operated and the operation unit 4 is lost, when the operation unit 4 and the manipulator 7 to which the endoscope 16 is attached become coordinated with each other, or when a particular switch disposed on the operation unit 4 is being depressed. In all other instances, only the first image A may be displayed.

In this manner, the unnecessary second image B is not displayed on the monitor 13 when there is no need to move the treatment tool 9 outside the field of view; thus, the first image A can be widely displayed on the monitor 13, and the ease of operation can be facilitated.

Moreover, in addition to the instances described above, the second image B may be displayed when it is detected that the treatment tool 9 outside the field of view has interfered with a surrounding object, such as surrounding tissue, for some reason. The detection of interference may be carried out by installing a contact sensor on the treatment tool 9.

Figure 7:
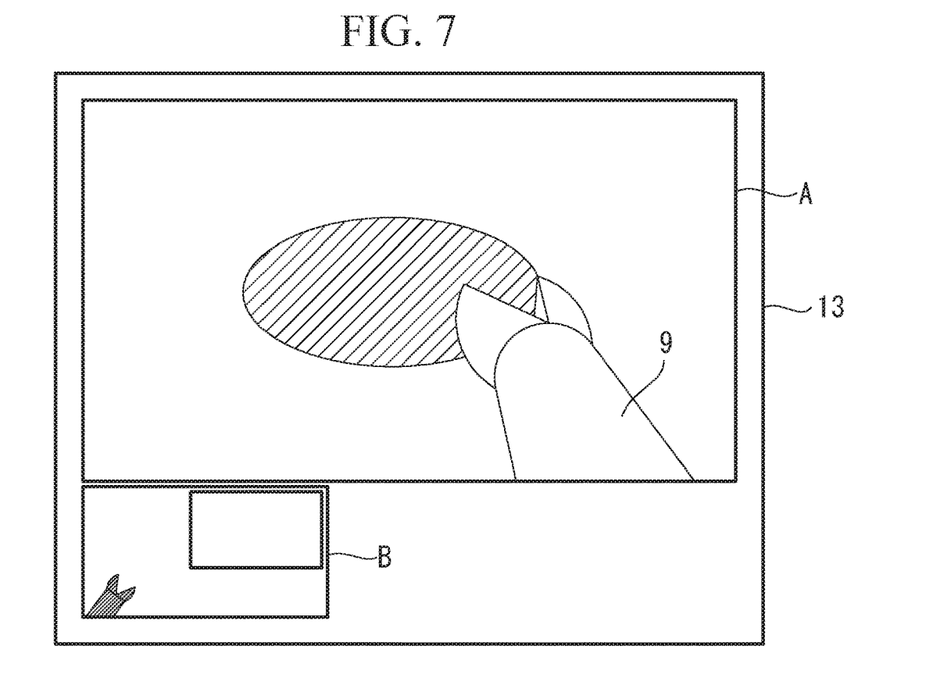
FIG. 7 is a diagram illustrating another example of a composite image generated in the image generating unit inside the controller of the medical manipulator system illustrated in FIG. 2.

In this embodiment, a copy of the first image A is added, as the image showing the viewing range of the endoscope 16, to the second image B; alternatively, as illustrated in FIG. 7, a frame indicating the viewing range may be displayed. Since the viewing range can be identified simply from the frame, the second image B can be configured easily by using a smaller amount of data.

Figure 8:
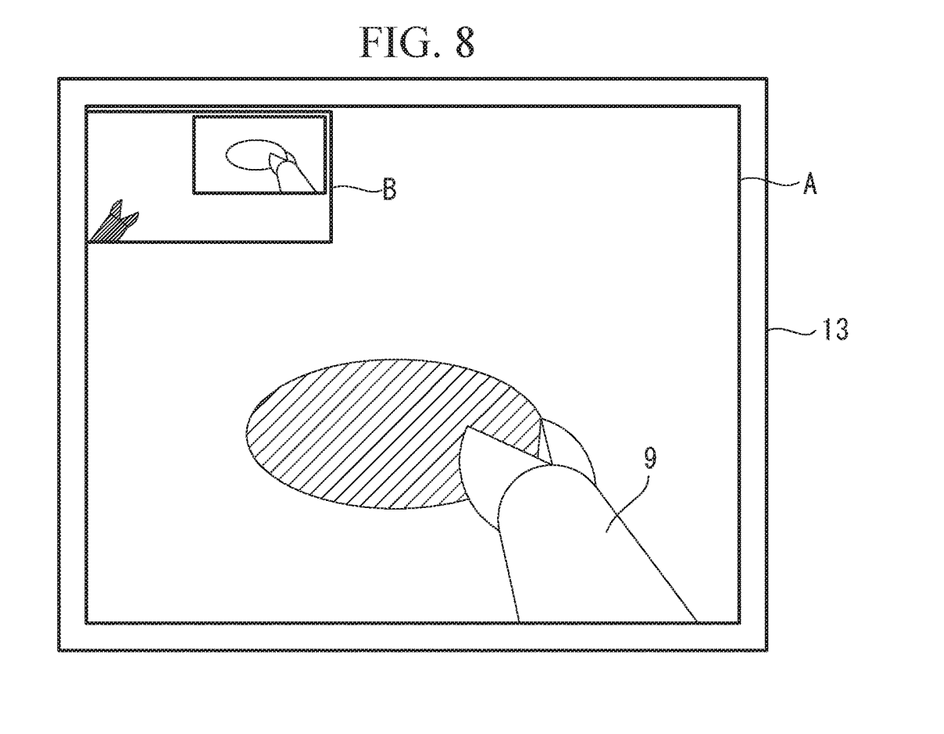
FIG. 8 is a diagram illustrating yet another example of a composite image generated in the image generating unit inside the controller of the medical manipulator system illustrated in FIG. 2.

In this embodiment, an example in which a composite image in which the second image B is disposed outside of the first image A so as to be juxtaposed with the first image A is described; alternatively, as illustrated in FIG. 8, a composite image in which the second image B is superimposed at a position inside the first image A so as not to obstruct the treatment may be generated.

Moreover, an image that shows the viewing range of the endoscope 16 is described as an example of the first image A; alternatively, a panoramic image that includes the endoscope 16 may be synthesized and used as the first image A.

Although the distance of the treatment tool 9 outside the field of view from the field of view is indicated by an icon indicating the treatment tool 9 outside the field of view and a frame or a copy of the first image displayed in the second image B, numerals indicating the distance may be displayed in addition.

The above-described embodiment also leads to the following aspects.

One aspect of the present invention is directed to a medical manipulator system that includes an endoscope; two or more manipulators each equipped with a treatment tool at a distal end thereof; an operation unit that operates the manipulators and the treatment tools; an image generating unit that generates a composite image by combining a first image within a field of view acquired by the endoscope and a second image that indicates out-of-field treatment tool information regarding the relative distance and direction between the field of view of the endoscope and the treatment tools outside the field of view; and a display unit that displays the composite image generated in the image generating unit.

According to this aspect, in the case where the endoscope is arranged to face the affected area, and the affected area is to be treated with a treatment tool at the distal end of one of the manipulators operated through the operating unit, the operated treatment tool and the affected area are placed within the field of view of the endoscope, and the treatment is performed while checking the relative positional relationship between the affected area and the treatment tool through the first image within the field of view acquired by the endoscope. In this case, in some instances, the user may wish to perform the treatment by switching the treatment tool to another treatment tool that is not currently operated but exists outside the field of view.

According to this embodiment, since the image generating unit generates a composite image by combining the first image within the field of view and the second image indicating the out-of-field treatment tool information, the user can easily judge, through the second image displayed on the display unit, the appropriateness of moving the treatment tool that exists outside the field of view.

In other words, since the out-of-field treatment tool information indicated in the second image contains information regarding the relative distance and direction between the field of view and the treatment tool outside the field of view, the user can judge that it is appropriate to move the treatment tool that exists outside the field of view when that treatment tool is close to the field of view. When the treatment tool is far from the field of view, the user can choose to first move the endoscope so that the treatment tool comes within the field of view and then operate the treatment tool, for example.

In the aspect described above, the second image may include a frame that indicates the field of view of the endoscope at a particular scale and a sign that indicates, at the same scale as the scale of the frame, a treatment tool outside the field of view, the sign being placed at the aforementioned distance and in the aforementioned direction with respect to the frame.

In this manner, since the sign indicating the treatment tool is disposed to show the relative positional relationship between the treatment tool and the frame that indicates the field of view, the relative distance and direction of the treatment tool outside the field of view relative to the field of view can be clearly indicated by using less information.

In the aspect described above, the out-of-field treatment tool information may be information that indicates whether the treatment tool outside the field of view is operable.

In this manner, the user can easily recognize, through the second image, whether or not the treatment tool outside the field of view is in an operable state. The operable state means that whether or not the manipulator to which the treatment tool outside the view of view is attached is coordinated with the operation unit, whether or not the treatment tool outside the field of view is grasping or retracting the tissue around the affected area, or the like.

In the aspect described above, the out-of-field treatment tool information may be information that indicates whether or not the treatment tool outside the field of view is in an operating state.

In this manner, when the treatment tool outside the field of view is in the operating state, the user can judge that the treatment tool is in an operable state.

In the aspect described above, the out-of-field treatment tool information may be acquired from operation command information for the treatment tool.

In this manner, the information including the distance and direction of the out-of-field treatment tool from the field of view can be easily acquired from the operation command information for the out-of-field treatment tool to be operated through the operation unit.

Another aspect of the present invention is directed to an image display method for a medical manipulator system that includes an endoscope, two or more manipulators each equipped with a treatment tool at a distal end thereof, and an operation unit that operates the manipulators and the treatment tools, the method including displaying a first image within a field of view acquired by the endoscope, and displaying, together with the first image, a second image that indicates out-of-field treatment tool information regarding the relative distance and direction between the field of view of the endoscope and the treatment tool outside the field of view.

In the aspect described above, whether or not the treatment tool outside the field of view displayed in the second image needs to be operated may be determined, and the second image may be displayed when it is determined that the treatment tool outside the field of view needs to be operated.

In this manner, when there is no need to operate the treatment tool outside the field of view, the second image is not displayed and the endoscopic image in the field of view can be displayed widely through the first image. Moreover, when it is necessary to operate the treatment tool outside the field of view, a composite image including the second image can be generated so that the user can easily judge the appropriateness of operating the treatment tool outside the field of view.

In the aspect described above, whether or not the treatment tool outside the field of view displayed in the second image interferes with another object may be determined, and the second image may be displayed when it is judged that the treatment tool outside the field of view interferes with another object.

In this manner, while the user operates the treatment tool in the field of view while viewing the first image, the second image is displayed when the treatment tool outside the field of view interferes with another object so as to inform the user that interference is happening outside the field of view.

According to the present invention, an advantage is afforded in that the user can easily judge the appropriateness of moving treatment tools that exist outside the field of view.

REFERENCE SIGNS LIST 1 medical manipulator system
4 operation unit
7 manipulator
9 treatment tool
13 monitor (display unit)
16 endoscope
18 image generating unit
A first image
B second image

The invention claimed is:

1. A medical manipulator system comprising:
an endoscope;
a first manipulator equipped with a first treatment tool at a distal end thereof;
a second manipulator equipped with a second treatment tool at a distal end thereof;
an operation unit being configured to receive an input from a user to control at least the first manipulator;
a display for the user to view; and
a controller configured to:
  acquire a first image taken by the endoscope, the first image containing the first treatment tool; and
  in response to determining that the second treatment tool does not exist in the first image:
    calculate a relative distance and a relative direction between the first treatment tool and the second treatment tool;
    determine whether or not the second manipulator is in an operable state relative to the operation unit;
    when the second manipulator is determined to be in the operable state, generate a second image showing the relative distance and the relative direction between the first treatment tool and the second treatment tool; and
    send the first image and the second image to the display.

2. The medical manipulator system according to claim 1, wherein the controller is configured to determine whether or not the second manipulator is in the operable state relative to the operation unit by determining whether the second treatment tool is coordinated with the operation unit.

3. The medical manipulator system according to claim 1, wherein the controller is configured to determine whether the second manipulator is in the operable state relative to the operation unit by determining whether or not the second treatment tool is grasping or retracting tissue around an affected area.

4. The medical manipulator system according to claim 1, wherein in response to the first image being rotated by an angle, the controller is configured to rotate the second image by the angle.

5. The medical manipulator system according to claim 1, wherein the controller is configured to display the second image in response to determining that it is necessary to move the second treatment tool, and display only the first image otherwise.

6. The medical manipulator system according to claim 1, further comprising a contact sensor,
 wherein the controller is configured to display the second image in response to the contact sensor detecting that the second treatment tool interferes with a surrounding object.

7. The medical manipulator system according to claim 1, wherein the controller is configured to generate a composite image in which the second image is superimposed at a position inside the first image.

8. A controller for a medical manipulator system comprising:
 one or more processors configured to:
  acquire a first image taken by an endoscope, the first image containing a first treatment tool of a first manipulator; and
 in response to determining that a second treatment tool of a second manipulator does not exist in the first image:
  calculate a relative distance and a relative direction between the first treatment tool and the second treatment tool,
  determine whether or not the second manipulator is in an operable state relative to the operation unit;
  when the second manipulator is determined to be in the operable state, generate a second image showing the relative distance and the relative direction between the first treatment tool and the second treatment tool, and
  send the first image and the second image to a display.

\* \* \* \* \*